US011633516B2

(12) United States Patent
Yu

(10) Patent No.: US 11,633,516 B2
(45) Date of Patent: Apr. 25, 2023

(54) AROMA CANDLE LIGHT

(71) Applicant: ShenZhen Fullwill Technology CO., LTD., Shenzhen (CN)

(72) Inventor: Junjie Yu, Guangdong (CN)

( * ) Notice: Subject to any disclaimer, the term of this patent is extended or adjusted under 35 U.S.C. 154(b) by 129 days.

(21) Appl. No.: 17/164,844

(22) Filed: Feb. 2, 2021

(65) Prior Publication Data

US 2021/0290812 A1    Sep. 23, 2021

(30) Foreign Application Priority Data

Mar. 20, 2020    (CN) .......................... 202020359822.X

(51) Int. Cl.
| | |
|---|---|
| *F21S 10/00* | (2006.01) |
| *A61L 9/14* | (2006.01) |
| *F21V 19/00* | (2006.01) |
| *F21V 23/04* | (2006.01) |
| *F21V 33/00* | (2006.01) |
| *B05B 17/00* | (2006.01) |
| *B05B 17/06* | (2006.01) |
| *F21S 10/04* | (2006.01) |
| *F21S 6/00* | (2006.01) |
| *B05B 14/00* | (2018.01) |

(52) U.S. Cl.
CPC ............ *A61L 9/14* (2013.01); *B05B 17/0646* (2013.01); *B05B 17/0676* (2013.01); *B05B 17/0684* (2013.01); *F21S 6/001* (2013.01); *F21S 10/04* (2013.01); *F21V 19/0015* (2013.01); *F21V 23/04* (2013.01); *F21V 33/0024* (2013.01); *A61L 2209/11* (2013.01); *A61L 2209/132* (2013.01); *B05B 14/00* (2018.02); *B05B 17/0607* (2013.01)

(58) Field of Classification Search
CPC ..... F21S 10/04; F21S 10/002; F21V 33/0044; F21W 2131/30; A61L 2209/12; A61L 9/14; A61L 2209/11; A61L 2209/132; B05B 17/0646; B05B 17/0676
See application file for complete search history.

(56) References Cited

U.S. PATENT DOCUMENTS

| | | | |
|---|---|---|---|
| 2011/0049266 A1* | 3/2011 | Jorgensen | A61L 9/14 239/338 |
| 2016/0298816 A1* | 10/2016 | Fang | F21S 10/04 |
| 2018/0177907 A1* | 6/2018 | Li | F21S 6/001 |

* cited by examiner

*Primary Examiner* — Y M. Quach Lee
(74) *Attorney, Agent, or Firm* — Prakash Nama; Global IP Services, PLLC

(57) ABSTRACT

This invention is a novel aroma candle light including a light body, a water spray formation channel, an ultrasonic device and a water tank; a water spray outlet is formed on a top part of the water spray formation channel; an LED light panel is fixedly mounted at the water spray outlet; the ultrasonic device includes an ultrasonic plate, an ultrasonic plate fixing member and a silicone rubber casing; the ultrasonic plate is disposed inside the silicone rubber casing; the ultrasonic plate fixing member has a top end which is provided with a recess; the silicone rubber casing is mounted inside the recess; the silicone rubber casing has a top part which is provided with a plurality of first guiding grooves; a plurality of second guiding grooves are formed inside the recess; the ultrasonic plate fixing member is disposed at an opening at a top part of the water tank.

10 Claims, 3 Drawing Sheets

AROMA CANDLE LIGHT

BACKGROUND OF THE INVENTION

The present invention relates to lighting technology and more specifically relates to a novel aroma candle light.

Currently, aroma candle lights use ultrasonic atomization device to diffuse perfume or essential oil; perfume is rapidly diffused to the entire space by heat, thereby achieving mind refreshing and air deodorizing effects. However, during diffusion by ultrasonic atomization, it is easy for some of the perfume and essential oil to flow back to the interior of the aroma candle light, resulting in difficult recycle and reuse, thus greatly reducing the usage rate of the perfume or essential oil and increasing the usage costs for using aroma candle lights.

BRIEF SUMMARY OF THE INVENTION

In view of the aforesaid disadvantages now present in the prior art, the present invention provides a novel aroma candle light which can reuse liquid in the aroma candle light many times, thereby increasing usage rate of the liquid inside the aroma candle light and reducing the usage costs incurred when using the product.

To attain this, the present invention provides the following technical solutions:

A novel aroma candle light comprising a light body; a water spray formation channel, an ultrasonic device and a water tank are fixed sequentially from top to bottom in the light body; a water spray outlet is formed on a top part of the water spray formation channel; an LED light panel is fixedly mounted at the water spray outlet; the water spray formation channel has an inner side wall which is provided with a plurality of water guiding grooves; the ultrasonic device comprises an ultrasonic plate, an ultrasonic plate fixing member and a silicone rubber casing; the ultrasonic plate is disposed inside the silicone rubber casing; the ultrasonic plate fixing member has a top end which is provided with a recess; the silicone rubber casing is mounted inside the recess; the silicone rubber casing has a top part which is provided with a plurality of first guiding grooves; a plurality of second guiding grooves are formed inside the recess; the second guiding grooves are positioned right under the first guiding grooves; the ultrasonic plate fixing member is disposed at an opening at a top part of the water tank.

Furthermore, the silicone rubber casing has a side wall which is provided with notches for guiding liquid from the first guiding grooves to the second guiding grooves.

Furthermore, the silicone rubber casing has a top end face which is in form of a slope surface with high middle part and low peripheral part.

Furthermore, the ultrasonic plate has a base which is provided with a water-absorbent cotton rod; a sleeve is fixedly mounted right under the opening; the cotton rod is disposed inside the sleeve.

Furthermore, a spring assembly is fixedly disposed inside the sleeve; the spring assembly comprises a connecting board and a spring; the connecting board is fixed on a side wall of the sleeve; the spring has a first end which is fixed to the connecting board and a second end which is fixed to a bottom of the water-absorbent cotton rod.

Furthermore, the LED light panel comprises a mounting board and a plurality of LED beads; the LED beads are fixed on a top part of the mounting board; an acute angle is formed between the LED beads and the mounting board.

Furthermore, a lampshade is disposed on the LED light panel; a first round hole which is same in size as the water spray outlet is provided on the lampshade at a position corresponding to the water spray outlet.

Furthermore, the light body is a cylinder with a top which is recessed diagonally downwards; the top is a bevel and recessed downwards to form a smooth surface; the smooth surface which is recessed downwards has a second round hole at center for receiving the lampshade.

Furthermore, the ultrasonic plate fixing member is mounted at the opening by snap connection.

Furthermore, a switch button is provided at an outer wall of the light body; a control panel is disposed in the light body; the switch button is connected with the control panel.

ADVANTAGEOUS EFFECTS

By using the LED light panel to illuminate the mist sprayed from the water spray outlet, the aroma candle light can produce a candle flame effect. By additionally providing the water spray formation channel, water mist could be formed in the channel with a certain length, thus attaining a candle flame effect, and further enhancing the candle flame effect produced by the aroma candle light. With the cooperation of the water guiding grooves, the slope surface, the first guiding grooves, the second guiding grooves and the water-absorbent cotton rod, it is possible to ensure that the liquid which flows back during diffusion of the aroma candle light could be absorbed by the water-absorbent cotton rod via the first guiding grooves and the second guiding grooves, thereby achieving recycle of the liquid and increasing the usage rate of the liquid in the aroma candle light. By providing the notches, it is possible to increase the efficiency of the return of the liquid from the first guiding grooves to the second guiding grooves. By providing the spring assembly, the water-absorbent cotton rod can abut against the ultrasonic plate under the action of the spring. By mounting the ultrasonic plate fixing member at the opening at the top part of the water tank, attachment or detachment of the ultrasonic plate fixing member to or from the water tank is more convenient.

Figure 1:
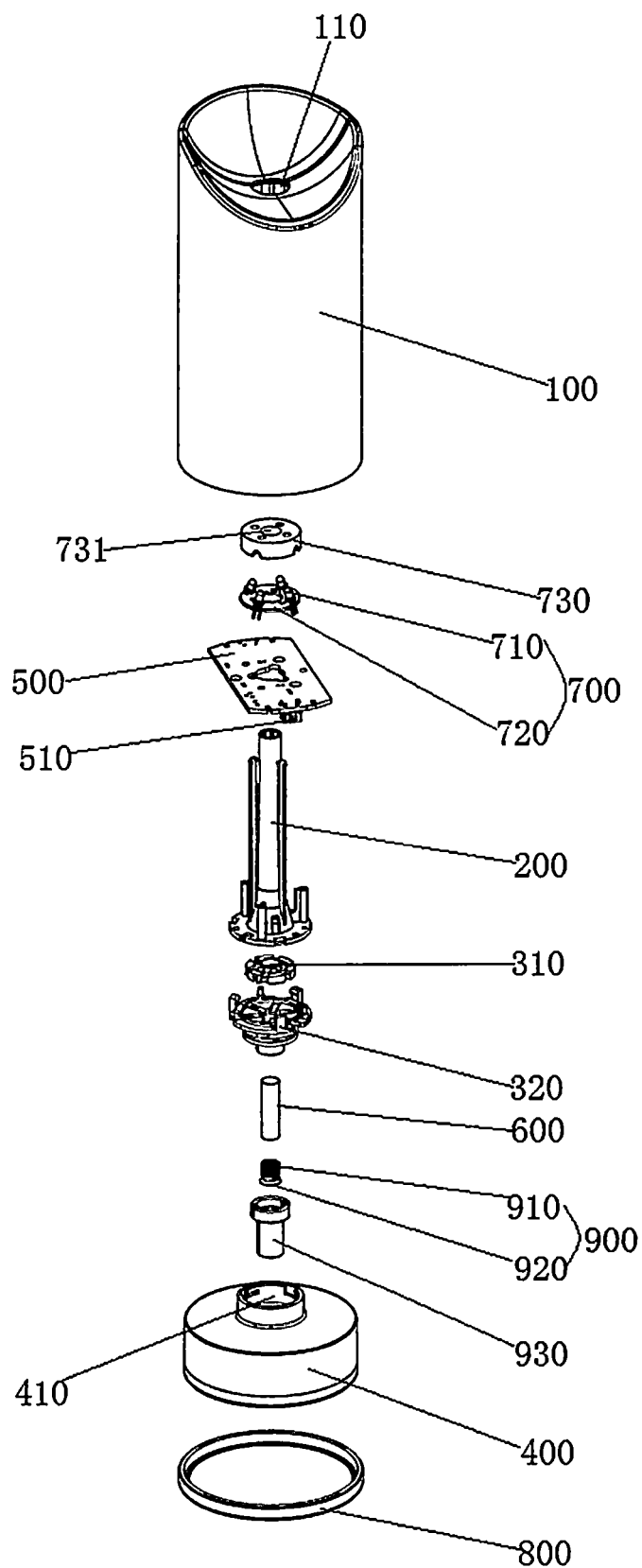
FIG. 1 is an exploded structural view of the present invention.

References in the figures: 100—light body; 110—second round hole; 200—water spray formation channel; 210—water spray outlet; 220—water guiding grooves; 300—ultrasonic device; 310—silicone rubber casing; 311—first guiding grooves; 312—notches; 320—ultrasonic plate fixing member; 321—recess; 322—second guiding grooves; 330—ultrasonic plate; 400—water tank; 410—opening; 500—control panel; 510—switch button; 600—water-absorbent cotton rod; 700—LED light panel; 710—LED beads; 720—mounting board; 730—lampshade; 731—first round hole; 800—cover; 900—spring assembly; 910—spring; 920—connecting board; 930—sleeve.

DETAILED DESCRIPTION OF THE INVENTION

Some embodiments of the present invention are further described in detail below. The embodiments are illustrated in the figures. Identical or like references throughout the description and the figures represent identical or like components or components having the same or similar functions. The embodiments described below with reference to the figures should be considered illustrative for the purpose of explaining the technical features of the present invention, and should not be considered as any limitation to the present invention.

In the present invention, it should be noted that directions or positional relationships indicated by terms such as "length", "width", "upper", "lower", "front", "rear", "left", "right", "vertical", "horizontal", "top", "bottom" should be understood based on the directions or positional relationships according to the figures, and should also be understood as merely means for simplification for the sake of easier illustration of the present invention. It is not meant or intended to mean that the devices or components concerned should have such specifically described directions, or should be configured or operated according to the specifically described directions, and hence should not be considered as any limitation to the present invention.

Further, terms like "first", "second" are used for illustrative purpose, and should not be understood as meaning or implying relative importance or as a subtle indication of a quantity of the described technical feature. Therefore, a feature defined by "first" or "second" may comprise, by obvious indication or subtle implication, one or more than one of said feature in terms of quantity. In the description, "a plurality of" means a quantity of two or above, unless otherwise specified.

In the embodiments of the present invention, unless otherwise specified, terms such as "install", "connect", "communicate" and "fix" should be understood broadly. For example, a fixed connection, a removable connection, or integral formation may be intended. Further, connection may be mechanical or electrical, direct or indirect through a medium, and may be an internal communication between two components or an interactive relationship between two components. A person skilled in this field of art should be able to understand the specific meaning of the terms described in the present invention according to the context of the practical situation described.

Figure 2:
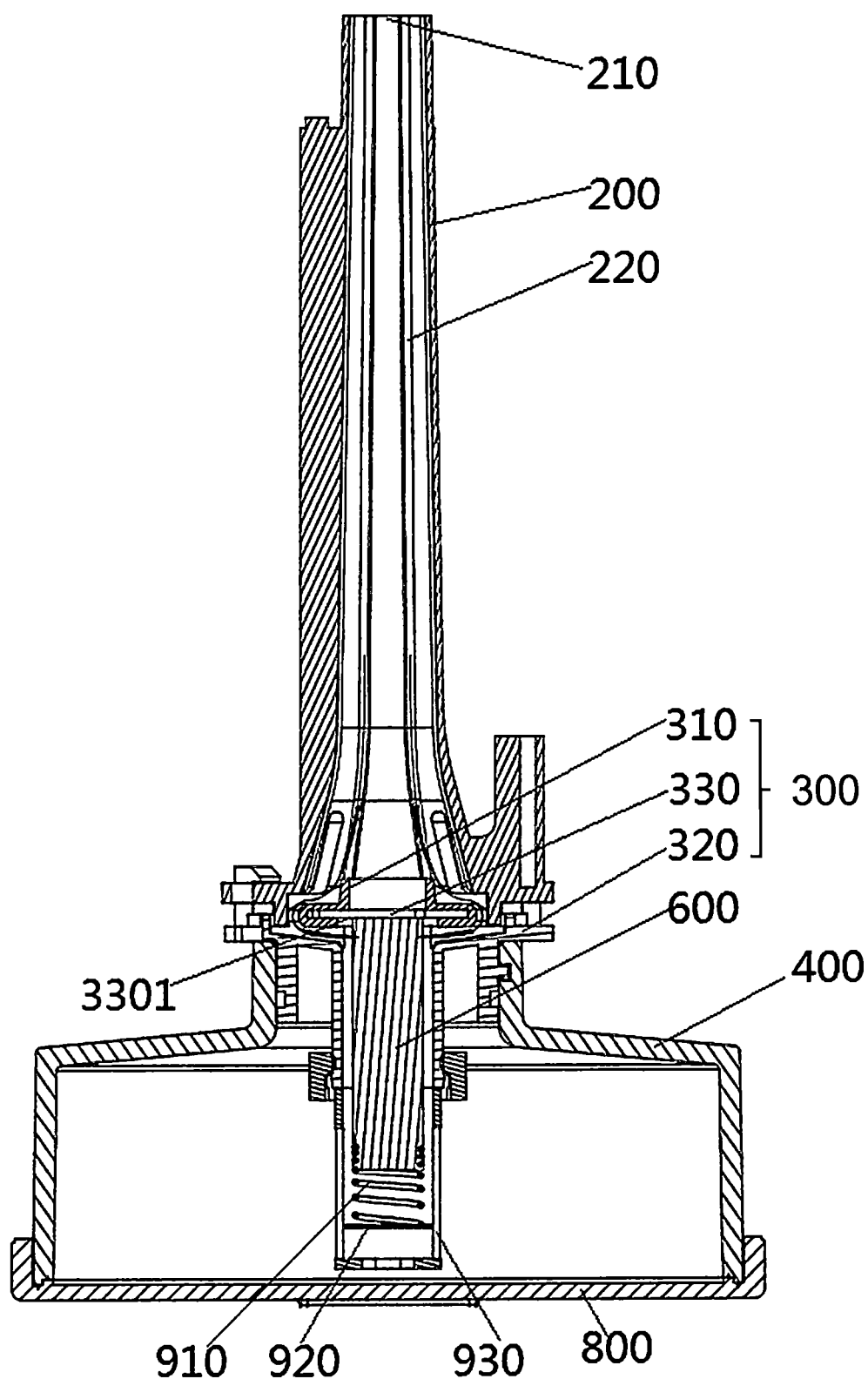
FIG. 2 is a sectional view showing the internal structure of the present invention.
Figure 3:
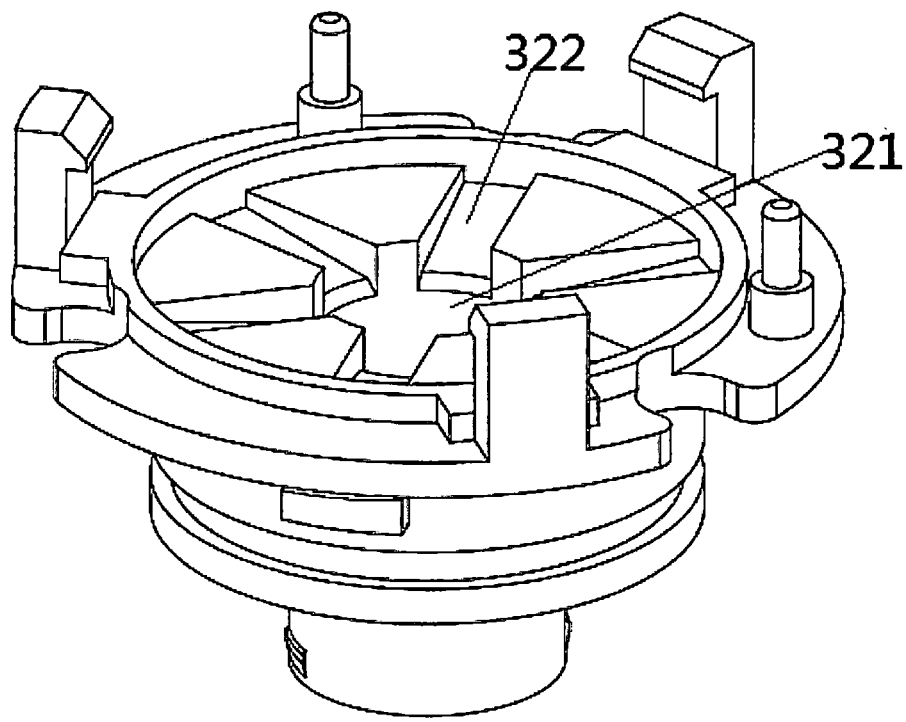
FIG. 3 is a schematic structural view of the ultrasonic plate fixing member.
Figure 4:
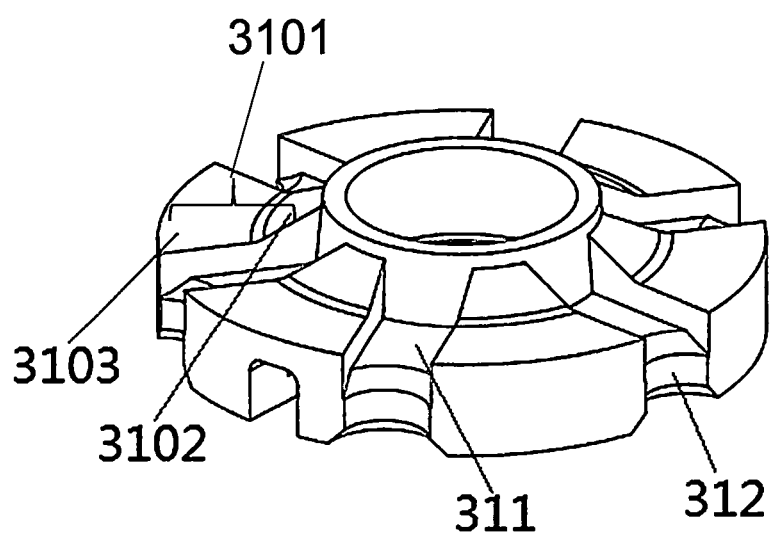
FIG. 4 is a schematic structural view of the silicone rubber casing of the present invention.

As illustrated in FIGS. 1-4, a novel aroma candle light comprises a light body 100; a water spray formation channel 200, an ultrasonic device 300 and a water tank 400 which are fixed sequentially from top to bottom in the light body 100. A water spray outlet 210 is formed on a top part of the water spray formation channel 200. An LED light panel 700 is fixedly mounted at the water spray outlet 210. The water spray formation channel 200 has an inner side wall which is provided with a plurality of water guiding grooves 220. The ultrasonic device 300 comprises an ultrasonic plate 330, an ultrasonic plate fixing member 320 and a silicone rubber casing 310. The ultrasonic plate 330 is disposed inside the silicone rubber casing 310. The ultrasonic plate fixing member 320 has a top end which is provided with a recess 321 for mounting the silicone rubber casing 310. The silicone rubber casing 310 has a top end face which is in form of a slope surface 3101 with high middle part 3102 and low peripheral part 3103. The slope surface is provided with a plurality of first guiding grooves 311. The first guiding grooves 311 are circumferentially and evenly arranged on the slope surface. A plurality of second guiding grooves 322 which slope gradually downwards from the periphery to a middle part of the recess 321 are formed in the recess 321. The second guiding grooves 322 are positioned right under the first guiding grooves 311, and the number of the second guiding grooves 322 corresponds to the number of the first guiding grooves 311. The silicone rubber casing 310 has a side wall which is provided with notches 312 for guiding liquid from the first guiding grooves 311 to the second guiding grooves 322. In this embodiment, the silicone rubber casing 310 could be substituted by a rubber casing; it is also possible to use other materials for substitution as long as protection of the ultrasonic plate 330 could be achieved. The ultrasonic plate fixing member 320 is mounted at an opening 410 at a top part of the water tank 400. The ultrasonic plate fixing member 320 has a bottom outer side wall which is formed with a protruding block. A hollow cylinder (not labelled in the figures) which opens at top thereof extends upwards from a top end face of the water tank 400. The hollow cylinder has an inner side wall, which is provided with a corresponding recess. The ultrasonic plate fixing member 320 is connected to the water tank 400 by snap connection between the protruding block and the recess. An annular cover 800 is fixedly connected to a bottom of the water tank 400. The cover 800 has a radius which is slightly larger than radius of the light body 100. The ultrasonic plate 330 has a base 3301 which is provided with a water-absorbent cotton rod 600. In this embodiment, the water-absorbent cotton rod 600 is in form of non-woven fabric cotton rod. In other embodiments, it is also possible to use cotton rods made of chemical fiber or other water conducting materials. A control panel 500 is disposed in the light body 100. A switch button 510 is provided at an outer wall of the light body 100. The ultrasonic plate 330 and the switch button 510 are both electrically connected with the control panel 500. The control panel 500 is further provided with electrical connecting port (not shown in the figures) which can connect to external power supply. In this embodiment, the switch button 510 is a touch button; it is also possible to substitute the touch button with a press button.

According to the present embodiment, the ultrasonic plate 330 has a base which is provided with the water-absorbent cotton rod 600. A sleeve 930 is fixedly mounted right under the opening 410. The cotton rod 600 is disposed inside the sleeve 930. A spring assembly 900 is fixedly disposed inside the sleeve 930. The spring assembly 900 comprises a connecting board 920 and a spring 910. The connecting board 920 is fixed on a side wall of the sleeve 930. The spring 910 has a first end which is fixed to the connecting board 920 and a second end which is fixed to a bottom of the water-absorbent cotton rod 600. Elongated grooves are provided on the side wall of the sleeve 930 to ensure liquid in the water tank 400 flows into the sleeve 930 via the elongated grooves.

According to the present embodiment, the LED light panel 700 comprises a mounting board 720 and a plurality of LED beads 710. The LED beads 710 are circumferentially and evenly fixed on a top part of the mounting board 720. The LED beads 710 face towards the water spray outlet 210, and an acute angle is formed between the LED beads 710 and the mounting board 720. In this embodiment, there are four LED beads. The number of LED beads 710 could be determined by actual needs.

According to the present embodiment, a lampshade 730 is disposed on the LED light panel 700. A first round hole 731 which is same in size as the water spray outlet 210 is provided on the lampshade 730 at a position corresponding to the water spray outlet 210.

According to the present embodiment, the light body 100 is a cylinder with a top which is recessed diagonally downwards. The top is a bevel and recessed downwards to form a smooth surface. The smooth surface which is recessed downwards has a second round hole 110 at center for receiving the lampshade 730.

Operating Principle:

When using the aroma candle light, under the action of the ultrasonic plate 330, the liquid in the water tank 400 is atomized for diffusion, and is diffused from the water spray outlet 210 via the water spray formation channel 200. Under the action by the LED beads 710, a candle flame effect is produced. During the movement of the atomized liquid in the water spray formation channel 200, part of the liquid flows back due to gravity; and the liquid which flows back sequentially passes through the water guiding grooves 220 to the top end face of the silicone rubber casing 310, and then to the first guiding grooves 311, and then to the second guiding grooves 322 via the notches 312, and thereby entering the water-absorbent cotton rod 600 which is connected with the ultrasonic plate 330. As a result, liquid recycle is achieved.

The above embodiments are only some of the preferred embodiments of the present invention. General changes or replacements made by a person skilled in this field of art in accordance with the scope of teachings of the present invention should also fall within the scope of protection of the present invention.

What is claimed is:

1. A novel aroma candle light comprising a light body, wherein a water spray formation channel, an ultrasonic device and a water tank are fixed sequentially from top to bottom in the light body; a water spray outlet is formed on a top part of the water spray formation channel; an LED light panel is fixedly mounted at the water spray outlet; the water spray formation channel has an inner side wall which is provided with a plurality of water guiding grooves; the ultrasonic device comprises an ultrasonic plate, an ultrasonic plate fixing member and a silicone rubber casing; the ultrasonic plate is disposed inside the silicone rubber casing; the ultrasonic plate fixing member has a top end which is provided with a recess; the silicone rubber casing is mounted inside the recess; the silicone rubber casing has a top part which is provided with a plurality of first guiding grooves; a plurality of second guiding grooves are formed inside the recess; the second guiding grooves are positioned right under the first guiding grooves; the ultrasonic plate fixing member is disposed at an opening at a top part of the water tank.

2. The novel aroma candle light as in claim 1, wherein the silicone rubber casing has a side wall which is provided with notches for guiding liquid from the first guiding grooves to the second guiding grooves.

3. The novel aroma candle light as in claim 2, wherein the silicone rubber casing has a top end face which is in form of a slope surface with high middle part and low peripheral part.

4. The novel aroma candle light as in claim 3, wherein the ultrasonic plate has a base which is provided with a water-absorbent cotton rod; a sleeve is fixedly mounted right under the opening; the cotton rod is disposed inside the sleeve.

5. The novel aroma candle light as in claim 4, wherein a spring assembly is fixedly disposed inside the sleeve; the spring assembly comprises a connecting board and a spring; the connecting board is fixed on a side wall of the sleeve; the spring has a first end which is fixed to the connecting board and a second end which is fixed to a bottom of the water-absorbent cotton rod.

6. The novel aroma candle light as in claim 5, wherein the LED light panel comprises a mounting board and a plurality of LED beads; the LED beads are fixed on a top part of the mounting board; an acute angle is formed between the LED beads and the mounting board.

7. The novel aroma candle light as in claim 6, wherein a lampshade is disposed on the LED light panel; a first round hole which is same in size as the water spray outlet is provided on the lampshade at a position corresponding to the water spray outlet.

8. The novel aroma candle light as in claim 7, wherein the light body is a cylinder with a top which is recessed diagonally downwards; the top is a bevel and recessed downwards to form a smooth surface; the smooth surface which is recessed downwards has a second round hole at center for receiving the lampshade.

9. The novel aroma candle light as in claim 8, wherein the ultrasonic plate fixing member is mounted at the opening by snap connection.

10. The novel aroma candle light as in claim 9, wherein a switch button is provided at an outer wall of the light body; a control panel is disposed in the light body; the switch button is connected with the control panel.

* * * * *